(12) United States Patent
Takai et al.

(10) Patent No.: US 7,977,522 B2
(45) Date of Patent: Jul. 12, 2011

(54) PROCESS OF PRODUCING OLEFINS

(75) Inventors: Toshihiro Takai, Nishinomiya (JP); Takeshi Kubota, Yokohama (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 897 days.

(21) Appl. No.: 11/883,540

(22) PCT Filed: Feb. 24, 2006

(86) PCT No.: PCT/JP2006/303493
§ 371 (c)(1), (2), (4) Date: Aug. 2, 2007

(87) PCT Pub. No.: WO2006/093058
PCT Pub. Date: Sep. 8, 2006

(65) Prior Publication Data
US 2010/0145126 A1 Jun. 10, 2010

(30) Foreign Application Priority Data

Mar. 3, 2005 (JP) .................................. 2005-058731
Apr. 14, 2005 (JP) .................................. 2005-117289

(51) Int. Cl.
*C07C 6/04* (2006.01)
(52) U.S. Cl. .......................... 585/643; 585/646; 585/647
(58) Field of Classification Search .................. 585/646, 585/643, 647
See application file for complete search history.

(56) References Cited

U.S. PATENT DOCUMENTS

| | | | |
|---|---|---|---|
| 3,536,777 A | | 10/1970 | Alkema et al. |
| 3,728,414 A | * | 4/1973 | Helden et al. ................. 585/646 |
| 3,786,112 A | * | 1/1974 | Reusser et al. ................. 585/644 |
| 4,575,575 A | | 3/1986 | Drake et al. |
| 4,684,760 A | | 8/1987 | Drake |
| 4,754,098 A | | 6/1988 | Drake |
| 4,795,734 A | | 1/1989 | Chauvin et al. |
| 4,884,760 A | | 12/1989 | Baggio et al. |

FOREIGN PATENT DOCUMENTS

| | | | |
|---|---|---|---|
| CA | 862816 | * | 2/1971 |
| CA | 862816 | A | 2/1971 |
| CA | 936878 | A | 11/1973 |
| CA | 936878 | A1 | 11/1973 |
| GB | 1117968 | | 4/1967 |
| GB | 1117968 | * | 6/1968 |
| GB | 1205677 | | 9/1970 |
| GB | 1338429 | | 11/1973 |
| JP | 47-003414 | A | 2/1972 |
| JP | 48-016482 | B1 | 5/1973 |
| JP | 59-001430 | A | 1/1984 |

OTHER PUBLICATIONS

Robert L. Banks et al., "New Developments and Concepts in Enhancing Activities of Heterogeneous Metathesis Catalysts", Journal of Molecular Catalysis, Jan. 3, 1985, pp. 117-131, vol. 28-No. 1, ISSN 0304-5102, Elsevier Sequoia S.A./Lausanne, The Netherlands.

The Examination Report from State Intellectual Property Office of the P.R. China issued in Applicant's corresponding Chinese Application No. GCC/P/2006/5908, dated Aug. 20, 2009.

Examination Report from European Patent Office issued in corresponding European Patent Convention application No. 06 714 632.4 dated Apr. 21, 2011.

* cited by examiner

*Primary Examiner* — Glenn A Caldarola
*Assistant Examiner* — Bradley Etherton
(74) *Attorney, Agent, or Firm* — Buchanan Ingersoll & Rooney PC

(57) ABSTRACT

A process of producing olefins by a metathesis reaction in a practical low temperature range by improving the reactivity of the catalyst is provided.

The process of producing olefins according to the present invention allows a metathesis reaction of olefins, which uses a catalyst containing metal elements such as tungsten, molybdenum, rhenium or the like, to proceed at an industrially sufficient reaction rate in a practical low temperature range, by using a compound containing at least one metal element selected from the metals of Group Ia (alkali metals), Group IIa (alkaline earth metals), Group IIb and Group IIIa as co-catalyst and allowing hydrogen gas to co-exist with the reaction raw material.

9 Claims, No Drawings

PROCESS OF PRODUCING OLEFINS

TECHNICAL FIELD

The present invention relates to a process of producing olefins by a metathesis reaction in which the catalytic reactivity is improved by allowing co-existence of hydrogen gas.

BACKGROUND ART

A metathesis reaction, in which homologous or heterologous olefins are reacted with each other to yield olefins having different structures, is highly beneficial since the reaction allows interconversion among ethylene, propylene, butene and the like that are produced from naphtha crackers at certain proportions, so as to cope with the changes in the demand structure of olefins.

The olefin metathesis reaction was found in 1931 to proceed at a high temperature of 725° C. without catalyst. However, the industrial value of the reaction was acknowledged only after a catalyst having an oxide of metal such as molybdenum, tungsten, rhenium or the like supported on a large surface area support was found. As the first exemplary metathesis reaction to use catalyst, a method of obtaining ethylene and 2-butene by a metathesis reaction between propylene and propylene using a catalyst comprising molybdenum oxide supported on γ-alumina, was developed by Phillips Inc. in 1964.

The metathesis reaction is reversible, and thus there exists an equilibrium composition. The equilibrium composition of the reaction to obtain propylene from ethylene and 2-butene becomes more advantageous in propylene production as the temperature is lower; therefore, lowering of the reaction temperature by improvement of the catalyst has been examined. Inter alia, a method of using a catalyst comprising tungsten oxide supported on silica and a co-catalyst of magnesium oxide was developed by Phillips Inc., and currently the method has been completed by Lummus Global, Inc. as a process for propylene production.

More particularly, it is reported in U.S. Pat. No. 4,575,575 (Patent Document 1) or Journal of Molecular Catalysis, Vol. 28, p. 117 (1985) (Non-Patent Document 1) that when a metathesis reaction between ethylene and 2-butene is carried out at 330° C. using a fixed bed flow apparatus only in the presence of a catalyst of silica-supported tungsten oxide, the conversion of butene is only 31%, while when magnesium oxide is used in combination as a co-catalyst, the conversion is enhanced to 67%.

Moreover, it is reported in U.S. Pat. No. 4,754,098 (Patent Document 2) that in the same metathesis reaction at 330° C., when a catalyst comprising magnesium oxide supported on γ-alumina is used, the conversion of butene is enhanced to 75%. It is also reported in U.S. Pat. No. 4,684,760 (Patent Document 3) that when a co-catalyst comprising magnesium oxide and lithium hydroxide supported on γ-alumina is used, the conversion of butene can be maintained to be 74% even at a much lower temperature of 270° C. In fact, there are needed facilities such as heating furnace and the like in order to achieve a reaction temperature of 270° C. in the industrial process, and it is desired to lower the reaction temperature to a temperature that is more simply achievable by steam heating, for example, up to about 200° C.

Furthermore, as an example of low temperature reaction catalysts, mention may be made of a catalyst comprising rhenium oxide supported on γ-alumina, developed by IFP (Institut Francais du Petrole). This catalyst is capable of driving the metathesis reaction at a reaction temperature around room temperature, that is, under pressurized conditions, using a liquefied mixture of ethylene and 2-butene as the starting material, as described in U.S. Pat. No. 4,795,734 (Patent Document 4). However, the liquefied raw material and the reaction product have low diffusibility in the pores of the catalyst, and thus deterioration of catalyst activity is severe compared with gas-phase reactions. In addition, since it is not practical to purge the liquefied gas in the reactor at every occurrence of regeneration in order to regenerate the deactivated catalyst, a moving-bed type reactor system in which the catalyst can be continuously withdrawn from the lower part of the fixed-bed reactor system and continuously regenerated has been designed. However, this method also involves complicated installation and has problems in the operational safety.

[Patent Document 1] U.S. Pat. No. 4,575,575
[Patent Document 2] U.S. Pat. No. 4,754,098
[Patent Document 3] U.S. Pat. No. 4,684,760
[Patent Document 4] U.S. Pat. No. 4,795,734
[Non-Patent Document 1] Journal of Molecular Catalysis, Vol. 28, p. 117 (1985)

DISCLOSURE OF THE INVENTION

It is an object of the present invention to solve the above-mentioned problems of the conventionally used methods in the related art, and thus to provide a process of producing olefins through a metathesis reaction in a practical low temperature range, wherein the catalytic reactivity is improved by allowing co-existence of hydrogen gas.

The present inventors have studied extensively to solve such problems, and as a result, they have found that with regard to an olefin metathesis reaction using a conventionally known catalyst containing a metal element such as tungsten, molybdenum, rhenium or the like, the metathesis reaction can be made to proceed in a practical low temperature range at an industrially sufficient reaction rate by using, together with the catalyst, a compound containing at least one metal element selected from the metals of Group Ia (alkali metals), Group IIa (alkaline earth metals), Group IIb and Group IIIa as the co-catalyst, and by allowing hydrogen gas to co-exist with the starting materials for reaction.

More specifically, with regard to a reaction between ethylene and 2-butene, the inventors have found that it is possible to reduce by-product such as pentene or hexene which are produced in addition to the targeted propylene, this founding having led to completion of this invention that is industrially valuable.

That is, the aspect of the present invention relates to a process of producing olefins by carrying out a metathesis reaction in which homologous or heterologous olefins are reacted with each other to yield olefins having different structures, using a catalyst containing at least one metal element selected from tungsten, molybdenum, rhenium, niobium, tantalum, vanadium, ruthenium, rhodium, iridium, osmium and nickel, wherein the process employs a compound containing at least one metal element selected from the metals of Group Ia (alkali metals), Group IIa (alkaline earth metals), Group IIb and Group IIIa as a co-catalyst, together with hydrogen gas.

According to the present invention, olefins can be produced by metathesis reactions with high yields and selectivities at low reaction temperatures that do not require special facilities such as heating furnace or the like, and also butene containing butadiene can be used as a starting material. Thus, olefins can be produced with significant advantages in the aspects of safety, processing and economics.

BEST MODE FOR CARRYING OUT THE INVENTION

The metathesis catalyst used in the present invention contains at least one selected from known metal elements such as tungsten, molybdenum, rhenium, niobium, tantalum, vanadium, ruthenium, rhodium, iridium, osmium, nickel and the like. Those having high activity are tungsten, molybdenum and rhenium, and among these, tungsten is particularly preferable.

The structure of the catalyst may be a simple substance in the solid state having a composition of oxide, sulfide hydroxide or the like of each metal, or may comprise the metal oxides, sulfides, hydroxides and the like supported on an inorganic compound having large surface area, which is called a support. The catalyst is preferably in an oxide form from the viewpoint that when used in a fixed-bed flow reaction, a deactivated catalyst can be regenerated by calcining in an air atmosphere.

Furthermore, since acidity of the support causes undesirable side reactions such as oligomerization of olefins and the like, any material not having acidity can be used for the support. More particularly, a support having a surface area of $10 \, m^2/g$ or more is preferred, and preferred examples thereof include silica, γ-alumina, titania and the like, with silica being selected as a suitable support particularly in view of having large surface area. In this case, the amount of the supported metal with respect to the support may be, in terms of oxide, in the range of 0.01% to 50%, and more preferably in the range of 0.1% to 20%.

The method of supporting an oxide, among the above-mentioned metal compounds, on a support may be any of the methods known in the art. In the case of a metal nitrate or hydroxide, or tungsten, molybdenum or rhenium, a supported catalyst can be obtained by impregnating a support with an aqueous solution provided by using a polyacid, an isopolyacid and an ammonium salt of a polyacid, or an ammonium salt of an isopolyacid of the respective metals as the starting material, or drying by evaporation, and calcining at a temperature of 300° C. or higher in an air atmosphere.

For the support, commercially available ones can be used without modification, but it is also possible to obtain a support as an oxide by neutralizing the corresponding metal salt with base by a known method, and calcining the resulting hydroxide.

When the support is to be obtained from a corresponding metal salt, it is also possible to employ a co-precipitation method which simultaneously carries out the synthesis of support and the supporting of metal by allowing co-existence of the metal salt which becomes the catalyst.

The shape of the support is not particularly limited, and any of spherical shape, cylindrical shape, extruded shape and crushed shape may be used. The size of the particle also may be selected in accordance with the size of the reactor in the range of 0.01 mm to 100 mm.

In addition, in order to solubilize the metal element compound such as tungsten, molybdenum, rhenium, niobium, tantalum, vanadium, ruthenium, rhodium, iridium, osmium or the like in an organic solvent, the catalyst may be a complex catalyst wherein an organic molecule called ligand is bonded to the catalyst. Further, in order to facilitate the recovery of such catalyst, the complex catalyst may be supported on a support.

The co-catalyst to be used in the present invention contains at least one metal element selected from the metals of Group Ia (alkali metals), Group IIa (alkaline earth metals), Group IIb and Group IIIc, and as the specific kind of the metal element, mention may be made of lithium, sodium, potassium, cesium, magnesium, calcium, strontium, barium, zinc, yttrium and the like.

U.S. Pat. No. 4,575,575, U.S. Pat. No. 4,754,098 and U.S. Pat. No. 4,684,760, all issued to Phillips Inc., describe co-catalysts containing magnesium oxide, but magnesium oxide is not necessarily essential in the present invention, and lithium, sodium and potassium are mentioned to be more preferred in the aspect of activity.

The metal compound to be used as the co-catalyst may be a simple substance in the solid state having a composition of oxide, hydroxide, nitrate, acetate or the like, or may comprise one of these metal compounds containing another metal compound, that is, a composite oxide such as hydrotalcite in which the respective oxides of aluminum and magnesium form a layered compound, or a solid solution of aluminum oxide and magnesium oxide. Alternatively, the co-catalyst may comprise oxides, composite oxides, hydroxides, nitrates, acetates or the like of these metals supported on an inorganic compound having large surface area, which is called a support.

Since acidity of the support causes undesirable side reactions such as oligomerization of olefins and the like, any material not having acidity even after having supported metal elements of Group Ia (alkali metals), Group IIa (alkaline earth metals), Group IIb and Group IIIa can be used for the support. More particularly, a support having a surface area of $10 \, m^2/g$ or more is preferred, and preferred examples thereof include γ-alumina, zirconia, titania and the like, with magnesium oxide possibly being used per se as a support in view of having large surface area. Particularly in view of chemical stability, γ-alumina is a preferred support. It is also preferable to use γ-alumina and magnesium oxide in combination, and to use a composite oxide of aluminum and magnesium. In this case, the amount of the supported metal with respect to the support may be, in terms of oxide, in the range of 0.01% to 50%, and more preferably in the range of 0.1% to 20%.

For the support, commercially available ones can be used without modification, but it is also possible to obtain a support as an oxide by basifying the corresponding metal salt by a known method, and calcining the resulting hydroxide.

The method of supporting an oxide, among the above-mentioned metal compounds, on a support may be any of the methods known in the art, and a supported catalyst can be obtained by impregnating a support with an aqueous solution of a nitrate or hydroxide of a metal or with an aqueous suspension of an oxide, or drying by evaporation, and calcining at a temperature of 300° C. or higher in an air environment.

When the support is to be obtained from a corresponding metal salt, it is also possible to employ a co-precipitation method which simultaneously carries out the synthesis of support and the supporting of metal by allowing co-existence of the metal salt which becomes the catalyst.

The shape of the support is not particularly limited, and any of spherical shape, cylindrical shape, extruded shape and crushed shape may be used. The size of the particle also may be selected in accordance with the size of the reactor in the range of 0.01 mm to 100 mm.

Furthermore, when a catalyst comprising a metal element such as tungsten or the like supported on a support and a co-catalyst comprising a metal element such as sodium, magnesium or the like supported on a support are used in combination, one kind of the support may simultaneously support the metal element such as tungsten or the like and the metal element such as sodium, magnesium or the like.

The amount of the co-catalyst with respect to the catalyst may be any amount between 0.1 to 20, but when the amount is excessively small, the effect of adding hydrogen is not exhibited, while when the amount is excessively large, the ratio of the catalyst is reduced, with the activity relative to the added amounts of the catalyst and the co-catalyst being lowered. Thus, it is not preferable. Further, when the fixed-bed flow apparatus is to be packed with the catalyst, as described in the Journal of Molecular Catalysis, Vol. 28, p. 117 (1985), the catalyst and the co-catalyst may be physically mixed and packed, or the co-catalyst and the catalyst may be packed in the described order from the side closer to the direction of raw material feeding. Mention may be also made of a method of combining the above.

The hydrogen added to the reaction is usually continuously supplied in the gas phase, but the supplying method is not particularly limited thereto. The hydrogen gas may be supplied intermittently such that the hydrogen gas is initially added at the beginning of the reaction, the supply is suspended in the reaction, and after a certain length of time, the hydrogen gas is supplied again, or in the case of a liquid phase reaction, the hydrogen gas may be dissolved in a solvent and supplied. In a recycle process, the hydrogen gas recovered from the top of the tower together with the low boiling point fraction may be supplied. At least, even if the hydrogen gas used for the reduction treatment of the catalyst is introduced to the reactor as residual hydrogen upon nitrogen purge, the effect of adding hydrogen would be observed in the very beginning, but the activity would be gradually lowered since there is no fresh supply of hydrogen, eventually the reaction results becoming the same as that of the case where hydrogen gas is not added. Thus, the sustained effect as obtained by the present invention cannot be expected.

The pressure of the hydrogen added is generally equal to the pressure in the reactor, but the pressure may be appropriately varied in accordance with the method of hydrogen supply.

The amount of the hydrogen gas to be added is, when the calculation for the raw materials to be supplied to the reactor is done in terms of gas, 0.1 to 80% by volume, preferably 0.2 to 50% by volume, of the total gas amount. When the amount of hydrogen is less than the lower limit of the range, the effect of addition may not be exhibited, while when the amount of hydrogen is excessively large, the partial pressure of the raw material olefins may be lowered, or the hydrogenation reaction of the olefins may simultaneously occur. Thus, it is not preferable.

The structure of the olefin to be used in the metathesis reaction according to the invention is not particularly limited, but in the case of being used for the purpose of improving the olefin balance in naphtha crackers, the metathesis reaction applies to lower olefins. Examples of the olefins that can be used as the raw material and the olefins that can be obtained include propylene from ethylene and 2-butene, propylene and 1-butene from ethylene and 2-pentene, propylene and 1-pentene from ethylene and 2-hexene, propylene and isobutene from ethylene and 2-methyl-2-butene, propylene and 3-methyl-1-butene from ethylene and 4-methyl-1-pentene, and the like. Further, since the reaction is a reversible reaction, the reverse reactions of the exemplified reactions are also effective.

These raw materials for reaction preferably consist of olefins only, but alkanes such as methane, ethane, propane, n-butane, isobutane, pentane, hexane and the like may be also contained. Further, terminal olefins such as 1-butene, 1-pentene, 1-hexene and the like may be contained in any amounts because they are isomerized to internal olefins by basic co-catalysts. The isobutene which co-exists in the case of obtaining propylene from ethylene and 2-butene reacts with the produced propylene to give 2-methyl-2-butene, and thus it is not desirable in the aspect of yield. However, since isobutene does not adversely affect the reaction per se, it may be contained in any amount.

The activity of the metathesis catalyst used in the invention is notably impaired by moisture, carbon dioxide, mercapto compounds, alcohols and carbonyl compounds, as is the same with the known art, thus impurities in the raw materials needed to be removed. The method of removing the impurities may be any of known methods such as distillation, adsorption, extraction, washing and the like.

When the invention is implemented by using two or more olefins as the raw materials, the amounts of the olefins used with respect to each other (weight ratio) are not particularly limited, but when one of the olefins is ethylene, it is desirable to use ethylene in excess. For example, in the case of a reaction for obtaining propylene from ethylene and 2-butene, the proportion of ethylene with respect to 2-butene is preferably 0.1 to 50, and more preferably about 0.5 to 5. When the proportion of ethylene is small, undesirable reactions between butene and butene occur in addition, while when the proportion of ethylene is excessively large, the energy required for the recovery of unreacted ethylene increases, and the size of the reactor itself should be increased. When two or more olefins are used, the olefin of larger proportion may be added altogether at the same time, or may be supplied in parts through an opening for feeding provided in the reactor at a halfway position, in addition to the inlet of the reactor.

The reaction temperature is also not particularly limited in the invention, but the temperature is preferably in the range of 100 to 500° C., and more preferably in the range of 130 to 350° C. When the reaction temperature is extremely low, the reaction rate is lowered, and the productivity of the reaction product is decreased. On the other hand, when the reaction temperature is extremely high, undesirable side reactions occur to increase side products or to deteriorate the catalyst, and thus it is not economical.

The reaction can be carried out in any of the states of reduced pressure, application of pressure and atmospheric pressure. From the viewpoint of reaction efficiency (reaction efficiency per unit volume), it is not desirable to carry out the reaction at an excessively low pressure. Typically, the preferred pressure is in the range of 0.1 to 200 atmospheres, and more preferably in the range of 0.5 to 100 atmospheres. Of course, the invention is not limited by these pressure ranges.

When the invention is carried out, the amount of catalyst used is not particularly limited. However, for example, in the case where the reaction is carried out using a fixed-bed flow apparatus, the value obtained by dividing the amount of raw materials supplied per hour (by weight) by the weight of only the catalyst containing tungsten or the like, without including the co-catalyst, that is, as expressed as WHSV, is preferably in the range of 1 to 2000/h, and more preferably in the range of 2 to 1000/h. When the WHSV is excessively low, the targeted olefin produced induces a successive metathesis reaction, thereby producing undesirable side products, while when the WHSV is excessively high, a sufficient reaction conversion cannot be obtained.

When the invention is to be implemented, it is also possible to carry out the reaction in a diluted state by adding a solvent or gas that is inert to the catalyst and reagents in the reaction system. Specifically, the above-mentioned alkanes such as methane, ethane, propane, butane and the like, or inert gases such as nitrogen, helium and the like can be used as the diluent.

When the invention is to be implemented, the invention can be carried out in any of the batch process, the semi-batch process and the continuous flow process. Further, the reaction can be also carried out in any of the liquid phase, the gas phase and the gas-liquid mixed phase. Preferably, it is recommended that the reaction is carried out in the gas phase from the viewpoint of reaction efficiency. The catalyst packing mode that can be used includes various modes such as fixed bed, fluidized bed, suspended bed, staged fixed bed and the like, and the reaction may be carried out in any of these modes.

After the reaction, the reaction products can be separated and recovered from the catalysts and the like by a known separation method. The targeted product olefins are separated from the reaction mixture by a known method such as distillation, extraction, adsorption or the like, and unreacted raw materials can be recovered and reused by recycling to the reaction system.

When the invention is to be implemented, it is desired to use the catalyst and co-catalyst after dehydrating them by known methods. In the case of fixed-bed reaction mode, the catalyst and co-catalyst may be maintained in a reactor at a temperature of 300° C. or higher for 10 or more minutes, while flowing in an inert gas such as nitrogen, helium or the like into the reactor. Especially when the metal element contained in the catalyst is tungsten or molybdenum, after maintaining the catalyst and the co-catalyst in the reactor, the catalyst may be subjected to a reduction treatment of flowing in a reducing gas such as carbon monoxide or hydrogen at a temperature of 300° C. or higher for 10 or more minutes, and subsequently to a treatment of flowing in an inert gas at a temperature of 300° C. or higher for 10 or more minutes, and the catalyst may be maintained at a predetermined reaction temperature. Since the present reaction is characterized in allowing the co-existence of hydrogen, when hydrogen is used in the reduction treatment, the used hydrogen may remain in the reactor.

When the catalyst activity is deteriorated over a certain period of time, the catalyst can be regenerated to recover the catalyst activity. In general, the olefin adsorbed on the catalyst is purged with nitrogen gas, and the catalyst is oxidized with air or nitrogen-diluted air at a temperature of 300° C. or higher. When the metal is tungsten or molybdenum, the catalyst can be subjected, after the oxidation, to reduction with a reducing gas such as hydrogen or carbon monoxide and can be reused.

In order to maintain the olefin output, two or three reactors may be arranged in parallel, and a merry-go-round mode in which while one of the reactors is being regenerated, the other one or two reactors are operated to carry out the metathesis reaction may be adopted. Furthermore, when there are three reactors, two of the reactors may be connected in series to reduce the fluctuation in the output. When the reaction is carried out in a fluidized-bed flow reaction mode or in a moving-bed reaction mode, all or part of the catalyst is withdrawn from the reactor continuously or intermittently, and a corresponding amount of the catalyst can be supplemented to maintain the activity at a certain level.

In a suspended-bed mode for a batch or continuous reaction, the catalyst is likewise separated and recovered, and if necessary, regenerated to be used again.

EXAMPLES

Example 1

0.83 g of ammonium metatungstate (Sigma-Aldrich Corporate) was dissolved in 100 ml of distilled water, and 5 g of silica gel Q-10 available from Fuji Silysia Chemical Ltd. (surface area 300 m$^2$/g, pore volume 1 ml/g, and 150 to 500 μm) was suspended therein with stirring at room temperature for 30 minutes. Subsequently, water was evaporated off in an evaporator. The resulting white solid was calcined under an air atmosphere at 550° C. for 6 hours. The obtained catalyst was referred to as WQ-10. 2 g of WQ-10 and 3.5 g of hydrotalcite (Kyowa Chemical Industry Co., Ltd., Kyowaad 500, 500 μm) were physically mixed and packed in a reactor manufactured by SUS, having an external diameter of 12 mm and a length of 40 cm, with the top and bottom of the reactor packed with α-alumina balls. The resulting reactor was used as a butene purifying tower. Next, 0.1 g of WQ-10 and 0.3 g of hydrotalcite were physically mixed and packed at the center of a reactor manufactured by SUS, having an external diameter of 10 mm and a length of 30 cm, with the top and bottom of the reactor packed with α-alumina balls. The resulting reactor was used as a reactor.

50 ml/min of nitrogen gas at ambient pressure was flowed in from the top of the reactor, and the gas exiting from the bottom of the reactor was flowed into the butene purifying tower from the bottom to the top, while the temperatures of the reactor and the butene purifying tower were all elevated to 550° C. and maintained for 1 hour. Subsequently, a gas mixture formed by adding 50 ml/min of hydrogen gas at ambient pressure to 50 ml/min of nitrogen gas at ambient pressure was flowed at the same temperature for 30 minutes. While flowing again 50 ml/min of nitrogen gas at ambient pressure, the butene purifying tower was cooled to 50° C., and the reactor was cooled to 250° C.

Trans-2-butene (99% purity, Takachiho Chemical Industrial Co., Ltd.) gas distilled over γ-alumina (Sumitomo Chemical Co., Ltd., NKHD-32) before use was flowed into the butene purifying tower from the bottom at ambient pressure at a rate of 2.3 ml/min. The purified trans-2-butene obtained from the top was combined with ethylene that was fed at ambient pressure at a rate of 6.1 ml/min and hydrogen that was fed at ambient pressure at a rate of 20 ml/min, and the mixture was fed to the reactor from the top in the gas phase. The gas mixture obtained from the bottom of the reactor was analyzed on-line by gas chromatography. Based on the composition taken 3 hours after the reaction initiation, the butene conversion calculated by deducting the total amount of trans-2-butene, cis-2-butene and 1-butene in the gas at the outlet, from the amount of supplied trans-2-butene was 75%. The propylene selectivity at this time based on butene was 97%, and a small amount of pentene was generated in addition. Further, propane was generated together with propylene, and the ratio of propane/propylene was 0.085. The reaction was further carried out for another 12 hours, but no decrease in the conversion was observed.

Example 2

The reaction was carried out in the same manner as in Example 1, except that the amount of the hydrogen gas at ambient pressure fed to the reactor was 5 ml/min. The butene conversion obtained by analyzing the gas at the outlet taken 3 hours after the reaction initiation was 75%. The propylene selectivity at this time based on butene was 98%, and a small amount of pentene was generated in addition. Further, propane was generated together with propylene, and the ratio of propane/propylene was 0.0094. The reaction was further carried out for another 12 hours, but no decrease in the conversion was observed.

Example 3

The reaction was carried out in the same manner as in Example 1, except that the amount of the hydrogen gas at ambient pressure fed to the reactor was 2 ml/min. The butene conversion obtained by analyzing the gas at the outlet taken 3 hours after the reaction initiation was 75%. The propylene selectivity at this time based on butene was 98%, and a small amount of pentene was generated in addition. Further, propane was generated together with propylene, and the ratio of propane/propylene was 0.0063. The reaction was further carried out for another 12 hours, but no decrease in the conversion was observed.

Example 4

The reaction was carried out in the same manner as in Example 3, except that the temperature of the reactor was set at 200° C. The butene conversion obtained by analyzing the gas at the outlet taken 3 hours after the reaction initiation was 75%. The propylene selectivity at this time based on butene was 98%, and a small amount of pentene was generated in addition. Further, propane was generated together with propylene, and the ratio of propane/propylene was 0.0032. The reaction was further carried out for another 12 hours, but no decrease in the conversion was observed.

addition. Further, propane was generated together with propylene, and the ratio of propane/propylene was 0.0069. The reaction was further carried out for another 12 hours, but no decrease in the conversion was observed.

Example 7

The reaction was carried out in the same manner as in Example 3, except that the kind of the co-catalyst packed in the reactor was changed to calcium oxide (Wako Pure Chemical Industries, Ltd., classified to 150 to 500 μm after compression molding). The butene conversion obtained by analyzing the gas at the outlet taken 1 hour after the reaction initiation was 78%. The propylene selectivity at this time based on butene was 98%, and a small amount of pentene was generated in addition. Further, propane was generated together with propylene, and the ratio of propane/propylene was 0.020.

Example 8

The reaction was carried out in the same manner as in Example 7, except that the temperature of the reactor was set at 200° C. The butene conversion obtained by analyzing the gas at the outlet taken 1 hour after the reaction initiation was 76%. The propylene selectivity at this time based on butene was 98%, and a small amount of pentene was generated in addition. Further, propane was generated together with propylene, and the ratio of propane/propylene was 0.0093.

TABLE 1

Propylene synthesis reaction performed using WQ-10 and hydrotalcite

| Example | Reaction Temperature | Flow Rate of Hydrogen | Butene Conversion | Propylene Selectivity | Propane/Propylene |
|---------|---------------------|----------------------|-------------------|----------------------|-------------------|
| 1 | 250° C. | 20 ml/min | 75% | 97% | 0.085 |
| 2 | 250° C. | 5 ml/min | 75% | 98% | 0.0094 |
| 3 | 250° C. | 2 ml/min | 75% | 98% | 0.0063 |
| 4 | 200° C. | 2 ml/min | 75% | 98% | 0.0032 |

Example 5

The reaction was carried out in the same manner as in Example 3, except that the kind of the co-catalyst packed in the reactor was changed to magnesium oxide (Kyowa Chemical Industry Co., Ltd., Kyowamag 150, classified to 150 to 500 μm after compression molding). The butene conversion obtained by analyzing the gas at the outlet taken 3 hours after the reaction initiation was 78%. The propylene selectivity at this time based on butene was 98%, and a small amount of pentene was generated in addition. Further, propane was generated together with propylene, and the ratio of propane/propylene was 0.011. The reaction was further carried out for another 12 hours, but no decrease in the conversion was observed.

Example 6

The reaction was carried out in the same manner as in Example 5, except that the temperature of the reactor was set at 200° C. The butene conversion obtained by analyzing the gas at the outlet taken 3 hours after the reaction initiation was 78%. The propylene selectivity at this time based on butene was 98%, and a small amount of pentene was generated in Example 9

The reaction was carried out in the same manner as in Example 3, except that the kind of the co-catalyst packed in the reactor was changed to yttrium oxide (classified to 150 to 500 μm after calcining at 550° C. the precipitate obtained by the addition of yttrium nitrate to aqueous ammonia, and compression molding). The butene conversion obtained by analyzing the gas at the outlet taken 3 hours after the reaction initiation was 77%. The propylene selectivity at this time based on butene was 98%, and a small amount of pentene was generated in addition. Further, propane was generated together with propylene, and the ratio of propane/propylene was 0.0024. The reaction was further carried out for another 12 hours, but no decrease in the conversion was observed.

Example 10

The reaction was carried out in the same manner as in Example 3, except that the kind of the co-catalyst packed in the reactor was changed to zinc oxide (Wako Pure Chemical Industries, Ltd., classified to 150 to 500 μm after compression molding), and also that the temperature of the reactor was set at 200° C. The butene conversion obtained by analyzing the gas at the outlet taken 1 hour after the reaction initiation was 32%. The propylene selectivity at this time based on butene was 90%, and a small amount of pentene was generated in addition. Further, propane was generated together with propylene, and the ratio of propane/propylene was 0.0013.

TABLE 2

Propylene synthesis reaction performed using WQ-10 and various co-catalysts

| Example | Reaction Temperature | Kind of Co-catalyst | Butene Conversion | Propylene Selectivity | Propane/Propylene |
|---------|---------------------|---------------------|-------------------|----------------------|-------------------|
| 5 | 250° C. | Magnesium oxide | 78% | 98% | 0.011 |
| 6 | 200° C. | Magnesium oxide | 78% | 98% | 0.0069 |
| 7 | 250° C. | Calcium oxide | 78% | 98% | 0.020 |
| 8 | 200° C. | Calcium oxide | 76% | 98% | 0.0093 |
| 9 | 250° C. | Yttrium oxide | 77% | 98% | 0.0024 |
| 10 | 200° C. | Zinc oxide | 32% | 90% | 0.0013 |

Example 11

3 g of γ-alumina (Sumitomo Chemical Co., Ltd., NKHD-32, surface area 250 m$^2$/g) was suspended in a solution dissolving 0.40 g of calcium hydroxide (Wako Pure Chemical Industries, Ltd.) in 100 ml of distilled water at room temperature with stirring for 30 minutes, and water was evaporated off in an evaporator. The resulting white solid was calcined under an air atmosphere at 550° C. for 6 hours. 0.3 g of the obtained γ-alumina-supported CaO was physically mixed with 0.1 g of WQ-10, and the mixture was packed at the center of a reactor manufactured by SUS, having an external diameter of 10 mm and a length of 30 cm, with the top and bottom of the reactor being packed with α-alumina balls. The resulting reactor was used as the reactor.

The reaction was carried out in the same manner as in Example 4, except that the above-described reactor was used. The butene conversion obtained by analyzing the gas at the outlet taken 3 hours after the reaction initiation was 74%. The propylene selectivity at this time based on butene was 97%, and a small amount of pentene was generated in addition. Further, propane was generated together with propylene, and the ratio of propane/propylene was 0.0018. The reaction was further carried out for another 12 hours, but no decrease in the conversion was observed.

Example 12

A co-catalyst was produced in the same manner as in Example 11, except that the amount of the calcium hydroxide supported on γ-alumina was 0.2 g, and the reaction was carried out in the same manner as in Example 4, except that the above-produced co-catalyst was used. The butene conversion obtained by analyzing the gas at the outlet taken 3 hours after the reaction initiation was 77%. The propylene selectivity at this time based on butene was 97%, and a small amount of pentene was generated in addition. Further, propane was generated together with propylene, and the ratio of propane/propylene was 0.0025. The reaction was further carried out for another 12 hours, but no decrease in the conversion was observed.

Example 13

A co-catalyst was produced in the same manner as in Example 11, except that the amount of the calcium hydroxide supported on γ-alumina was 0.1 g, and the reaction was carried out in the same manner as in Example 4, except that the above-produced co-catalyst was used. The butene conversion obtained by analyzing the gas at the outlet taken 3 hours after the reaction initiation was 75%. The propylene selectivity at this time based on butene was 96%, and a small amount of pentene was generated in addition. Further, propane was generated together with propylene, and the ratio of propane/propylene was 0.0022. The reaction was further carried out for another 12 hours, but no decrease in the conversion was observed.

Example 14

A co-catalyst was produced in the same manner as in Example 11, except that the compound supported on γ-alumina was 0.55 g of magnesium nitrate (Wako Pure Chemical Industries, Ltd.), and the reaction was carried out in the same manner as in Example 5, except that the above-produced co-catalyst was used. The butene conversion obtained by analyzing the gas at the outlet taken 3 hours after the reaction initiation was 16%. The propylene selectivity at this time based on butene was 87%, and a small amount of pentene was generated in addition. Further, propane was generated together with propylene, and the ratio of propane/propylene was 0.0036. The reaction was further carried out for another 12 hours, but no decrease in the conversion was observed.

Example 15

A co-catalyst was produced in the same manner as in Example 11, except that the compound supported on γ-alumina was 0.35 g of zinc nitrate (Wako Pure Chemical Industries, Ltd.), and the reaction was carried out in the same manner as in Example 4, except that the above-produced co-catalyst was used. The butene conversion obtained by analyzing the gas at the outlet taken 3 hours after the reaction initiation was 66%. The propylene selectivity at this time based on butene was 94%, and a small amount of pentene was generated in addition. Further, propane was generated together with propylene, and the ratio of propane/propylene was 0.0016. The reaction was further carried out for another 12 hours, but no decrease in the conversion was observed.

Example 16

A co-catalyst was produced in the same manner as in Example 11, except that the compounds supported on γ-alumina were 0.35 g of zinc nitrate (Wako Pure Chemical Industries, Ltd.) and 0.038 g of sodium hydroxide (Wako Pure Chemical Industries, Ltd.), and the reaction was carried out in the same manner as in Example 4, except that the above-produced co-catalyst was used. The butene conversion obtained by analyzing the gas at the outlet taken 3 hours after the reaction initiation was 76%. The propylene selectivity at this time based on butene was 95%, and a small amount of pentene was generated in addition. Further, propane was generated together with propylene, and the ratio of propane/propylene was 0.0021. The reaction was further carried out for another 12 hours, but no decrease in the conversion was observed.

Example 17

A co-catalyst was produced in the same manner as in Example 11, except that the compound supported on γ-alumina was 0.076 g of sodium hydroxide (Wako Pure Chemical Industries, Ltd.), and the reaction was carried out in the same manner as in Example 4, except that the above-produced co-catalyst was used. The butene conversion obtained by analyzing the gas at the outlet taken 1 hour after the reaction initiation was 75%. The propylene selectivity at this time based on butene was 98%, and a small amount of pentene was generated in addition. Further, propane was generated together with propylene, and the ratio of propane/propylene was 0.0033.

Example 18

A co-catalyst was produced in the same manner as in Example 11, except that the compound supported on γ-alumina was 0.038 g of sodium hydroxide (Wako Pure Chemical Industries, Ltd.), and the reaction was carried out in the same manner as in Example 3, except that the above-produced co-catalyst was used. The butene conversion obtained by analyzing the gas at the outlet taken 3 hours after the reaction initiation was 76%. The propylene selectivity at this time based on butene was 97%, and a small amount of pentene was generated in addition. Further, propane was generated together with propylene, and the ratio of propane/propylene was 0.001. The reaction was further carried out for another 12 hours, but no decrease in the conversion was observed.

TABLE 3

Propylene synthesis reaction performed using WQ-10 and various alumina-supported co-catalysts

| Ex. | Compound supported on alumina | Weight used for supporting(*) | Butene Conversion | Propylene Selectivity | Propane/Propylene |
|---|---|---|---|---|---|
| 11 | Calcium hydroxide | 0.4 g | 74% | 97% | 0.0018 |
| 12 | Calcium hydroxide | 0.2 g | 77% | 97% | 0.0025 |
| 13 | Calcium hydroxide | 0.1 g | 75% | 96% | 0.0022 |
| 14 | Magnesium nitrate | 0.55 g | 16% | 87% | 0.0036 |
| 15 | Zinc nitrate | 0.35 g | 66% | 94% | 0.0016 |
| 16 | Zinc nitrate and sodium hydroxide | 0.35 g and 0.038 g, respectively | 76% | 95% | 0.0021 |
| 17 | Sodium hydroxide | 0.076 g | 75% | 98% | 0.0033 |
| 18 | Sodium hydroxide | 0.038 g | 76% | 97% | 0.0010 |

(*)Amount used based on 3 g of alumina

Example 19

A co-catalyst was produced in the same manner as in Example 18, except that the reaction temperature was set at 200° C., and the reaction was carried out in the same manner as in Example 4, except that the above-produced co-catalyst was used. The butene conversion obtained by analyzing the gas at the outlet taken 3 hours after the reaction initiation was 78%. The propylene selectivity at this time based on butene was 98%, and a small amount of pentene was generated in addition. Further, propane was generated together with propylene, and the ratio of propane/propylene was 0.00081. The reaction was further carried out for another 12 hours, but no decrease in the conversion was observed.

Example 20

A co-catalyst was produced in the same manner as in Example 18, except that the reaction temperature was set at 175° C., and the reaction was carried out in the same manner as in Example 4, except that the above-produced co-catalyst was used. The butene conversion obtained by analyzing the gas at the outlet taken 3 hours after the reaction initiation was 74%. The propylene selectivity at this time based on butene was 97%, and a small amount of pentene was generated in addition. Further, propane was generated together with propylene, and the ratio of propane/propylene was 0.00053. The reaction was further carried out for another 12 hours, but no decrease in the conversion was observed.

Example 21

A co-catalyst was produced in the same manner as in Example 18, except that the reaction temperature was set at 150° C., and the reaction was carried out in the same manner as in Example 4, except that the above-produced co-catalyst was used. The butene conversion obtained by analyzing the gas at the outlet taken 1 hour after the reaction initiation was 30%. The propylene selectivity at this time based on butene was 92%, and a small amount of pentene was generated in addition. Further, propane was generated together with propylene, and the ratio of propane/propylene was 0.0029.

Example 22

A co-catalyst was produced in the same manner as in Example 11, except that the compound supported on γ-alumina was 0.019 g of sodium hydroxide (Wako Pure Chemical Industries, Ltd.), and the reaction was carried out in the same manner as in Example 4, except that the above-produced co-catalyst was used. The butene conversion obtained by analyzing the gas at the outlet taken 3 hours after the reaction initiation was 78%. The propylene selectivity at this time based on butene was 98%, and a small amount of pentene was generated in addition. Further, propane was generated together with propylene, and the ratio of propane/propylene was 0.0067. The reaction was further carried out for another 12 hours, but no decrease in the conversion was observed.

Example 23

A co-catalyst was produced in the same manner as in Example 19, except that instead of γ-alumina, zirconium hydroxide which was obtained by adding zirconium nitrate to aqueous ammonia, washing the resulting zirconium hydroxide in the gel state with water, and then drying it at 100° C. was used, and the reaction was carried out in the same manner as in Example 4, except that the obtained zirconia-supported $Na_2O$ was used as the co-catalyst. The butene conversion obtained by analyzing the gas at the outlet taken 3 hours after the reaction initiation was 78%. The propylene selectivity at this time based on butene was 98%, and a small amount of pentene was generated in addition. Further, propane was generated together with propylene, and the ratio of propane/propylene was 0.0045. The reaction was further carried out for another 12 hours, but no decrease in the conversion was observed.

Example 24

A co-catalyst was produced in the same manner as in Example 23, except that the reaction temperature was set at 175° C., and the reaction was carried out in the same manner as in Example 4, except that the above-produced co-catalyst was used. The butene conversion obtained by analyzing the gas at the outlet taken 1 hour after the reaction initiation was 58%. The propylene selectivity at this time based on butene was 94%, and a small amount of pentene was generated in addition. Further, propane was generated together with propylene, and the ratio of propane/propylene was 0.0015.

TABLE 4

Propylene synthesis reaction performed using WQ-10 and co-catalysts comprising $Na_2O$ supported on various supports

| Ex. | Reaction Temp. | Type of Support | Weight of NaOH used for support(*) | Butene Conversion | Propylene Selectivity | Propane/ Propylene |
|---|---|---|---|---|---|---|
| 19 | 200° C. | Alumina | 0.038 g | 78% | 98% | 0.00081 |
| 20 | 175° C. | Alumina | 0.038 g | 74% | 97% | 0.00053 |
| 21 | 150° C. | Alumina | 0.038 g | 30% | 92% | 0.0029 |
| 22 | 200° C. | Alumina | 0.019 g | 78% | 98% | 0.0067 |
| 23 | 200° C. | Zirconia | 0.038 g | 78% | 98% | 0.0045 |
| 24 | 175° C. | Zirconia | 0.038 g | 58% | 94% | 0.0015 |

(*)Amount used based on 3 g of the support

Example 25

A co-catalyst was produced in the same manner as in Example 11, except that the compound supported on γ-alumina was 0.064 g of potassium nitrate (Wako Pure Chemical Industries, Ltd.), and the reaction was carried out in the same manner as in Example 3, except that the above-produced co-catalyst was used. The butene conversion obtained by analyzing the gas at the outlet taken 3 hours after the reaction initiation was 76%. The propylene selectivity at this time based on butene was 98%, and a small amount of pentene was generated in addition. Further, propane was generated together with propylene, and the ratio of propane/propylene was 0.0020. The reaction was further carried out for another 12 hours, but no decrease in the conversion was observed.

Example 26

A co-catalyst was produced in the same manner as in Example 25, except that the amount of the compound supported on γ-alumina was 0.128 g, and the reaction was carried out in the same manner as in Example 3, except that the above-produced co-catalyst was used. The butene conversion obtained by analyzing the gas at the outlet taken 3 hours after the reaction initiation was 77%. The propylene selectivity at this time based on butene was 96%, and a small amount of pentene was generated in addition. Further, propane was generated together with propylene, and the ratio of propane/propylene was 0.00057. The reaction was further carried out for another 12 hours, but no decrease in the conversion was observed.

Example 27

A co-catalyst was produced in the same manner as in Example 11, except that the compound supported on γ-alumina was 0.041 g of cesium nitrate (Wako Pure Chemical Industries, Ltd.), and the reaction was carried out in the same manner as in Example 4, except that the above-produced co-catalyst was used. The butene conversion obtained by analyzing the gas at the outlet taken 3 hours after the reaction initiation was 76%. The propylene selectivity at this time based on butene was 98%, and a small amount of pentene was generated in addition. Further, propane was generated together with propylene, and the ratio of propane/propylene was 0.00095. The reaction was further carried out for another 12 hours, but no decrease in the conversion was observed.

Example 28

A co-catalyst was produced in the same manner as in Example 27, except that the amount of the compound supported on γ-alumina was 0.082 g, and the reaction was carried out in the same manner as in Example 4, except that the above-produced co-catalyst was used. The butene conversion obtained by analyzing the gas at the outlet taken 3 hours after the reaction initiation was 75%. The propylene selectivity at this time based on butene was 97%, and a small amount of pentene was generated in addition. Further, propane was generated together with propylene, and the ratio of propane/propylene was 0.0013. The reaction was further carried out for another 12 hours, but no decrease in the conversion was observed.

TABLE 5

Propylene synthesis reaction performed using WQ-10 and various alumina-supported co-catalysts

| Example | Compound supported on alumina | Weight used for supporting(*) | Butene Conversion | Propylene Selectivity | Propane/Propylene |
|---|---|---|---|---|---|
| 25 | Potassium nitrate | 0.064 g | 76% | 98% | 0.0020 |
| 26 | Potassium nitrate | 0.128 g | 77% | 96% | 0.00057 |
| 27 | Cesium nitrate | 0.041 g | 76% | 98% | 0.00095 |
| 28 | Cesium nitrate | 0.082 g | 75% | 97% | 0.0013 |

(*)Amount used based on 3 g of alumina

Example 29

The reaction was carried out in the same manner as in Example 4, except that the reaction raw material used was changed from trans-2-butene to 1-butene (Takachiho Chemical Industrial Co., Ltd., purity 99.5%). The butene conversion obtained by analyzing the gas at the outlet taken 3 hours after the reaction initiation was 76%. The propylene selectivity at this time based on butene was 98%, and a small amount of pentene was generated in addition. Further, propane was generated together with propylene, and the ratio of propane/propylene was 0.0041. The reaction was further carried out for another 12 hours, but no decrease in the conversion was observed.

TABLE 6

Propylene synthesis reaction performed at 200° C. using WQ-10 and hydrotalcite and using various butanes

| Example | Butene used as raw material | Butene Conversion | Propylene Selectivity | Propane/Propylene |
|---|---|---|---|---|
| 4 | Trans-2-butene | 75% | 98% | 0.0032 |
| 29 | 1-Butene | 76% | 98% | 0.0041 |

Example 30

The reaction was carried out in the same manner as in Example 3. The butene conversion obtained by analyzing the gas at the outlet taken 3 hours after the reaction initiation was 75%. The propylene selectivity at this time based on butene was 98%, and a small amount of pentene was generated in addition. Further, propane was generated together with propylene, and the ratio of propane/propylene was 0.0063. After 3 hours after reaction initiation, the hydrogen supply to the reactor was suspended, and the reaction was continued as such. The butene conversion obtained by analyzing the gas at the outlet taken 1 hour after the suspension of the hydrogen gas supply decreased to 48%. Further, the butene conversion obtained by analyzing the gas at the outlet taken 5 hours after the suspension of the hydrogen gas supply remained to be 48%. The hydrogen gas supply to the reactor was resumed, and the reaction was continued. The butene conversion obtained by analyzing the gas at the outlet taken 3 hours after the resumption of the hydrogen gas supply improved to 72%. Further, the butene conversion obtained by analyzing the gas at the outlet taken 8 hours after the resumption of the hydrogen gas supply was 74%.

TABLE 7

Switching test with addition of hydrogen at 250° C. (Example 30)

| Example | Sampling Time | Butene Conversion |
|---|---|---|
| 3 | 3 hours after reaction initiation | 75% |
| 30 | 3 hours after reaction initiation | 75% |
|  | 4 hours after reaction initiation (1 hour after suspension of hydrogen gas supply) | 48% |
|  | 8 hours after reaction initiation (5 hours after suspension of hydrogen gas supply) | 48% |
|  | 11 hours after reaction initiation (3 hours after hydrogen gas resupply) | 72% |
|  | 16 hours after reaction initiation (8 hours after hydrogen gas resupply) | 74% |

Example 31

0.49 g of ammonium metamolybdate (Sigma-Aldrich Corporate) was dissolved in 100 ml of distilled water, and 5 g of silica gel Q-15 available from Fuji Silysia Chemical, Ltd. (surface area 200 m$^2$/g, pore volume 1 ml/g, and 150 to 500 μm) was suspended therein with stirring at room temperature for 30 minutes. Subsequently, water was evaporated off in an evaporator. The resulting white solid was calcined under an air atmosphere at 550° C. for 6 hours. The obtained catalyst was referred to as MoQ-15. 2 g of WQ-10 and 3.5 g of hydrotalcite (Kyowa Chemical Industry Co., Ltd., Kyowaad 500, 500 μm) were physically mixed and packed in a reactor manufactured by SUS, having an external diameter of 12 mm and a length of 40 cm, with the top and bottom of the reactor packed with α-alumina balls. The resulting reactor was used as a butene purifying tower. Next, 0.1 g of MoQ-15 and 0.3 g of hydrotalcite were physically mixed and packed at the center of a reactor manufactured by SUS, having an external diameter of 10 mm and a length of 30 cm, with the top and bottom of the reactor packed with α-alumina balls. The resulting reactor was used as a reactor.

The reaction was carried out in the same manner as in Example 3, except that the temperature of the reactor was set at 300° C. The butene conversion obtained by analyzing the gas at the outlet taken 1 hour after the reaction initiation was 47%. The propylene selectivity at this time based on butene was 89%, and a small amount of pentene was generated in addition. Further, propane was generated together with propylene, and the ratio of propane/propylene was 0.015.

Example 32

The reaction was carried out in the same manner as in Example 31, except that the temperature of the reactor was set at 350° C. The butene conversion obtained by analyzing the gas at the outlet taken 1 hour after the reaction initiation was 53%. The propylene selectivity at this time based on butene was 90%, and a small amount of pentene was generated in addition. Further, propane was generated together with propylene, and the ratio of propane/propylene was 0.0014.

TABLE 8

Propylene synthesis reaction performed using MoQ-15 and hydrotalcite

| Example | Reaction Temperature | Butene Conversion | Propylene Selectivity | Propane/Propylene |
|---|---|---|---|---|
| 31 | 300° C. | 47% | 89% | 0.015 |
| 32 | 350° C. | 53% | 90% | 0.0014 |

Example 33

For Example 1, 0.6 g of WQ-10 and 2.4 g of hydrotalcite were physically mixed and packed at the center of a reactor manufactured by SUS, having an external diameter of 18 mm and a length of 400 mm. The top and bottom of the reactor was packed with α-alumina balls, and this was used as the reactor. 100 ml/min of nitrogen gas at ambient pressure was flowed in from the top of the reactor, and the gas exiting from the bottom of the reactor was flowed into the butene purifying tower from the bottom to the top. The temperatures of the reactor and the butene purifying tower were all elevated to 500° C. and maintained for 1 hour. Subsequently, 100 ml/min of hydrogen gas at ambient pressure was flowed at the same temperature for 120 minutes. While flowing 50 ml/min of nitrogen gas at ambient pressure and 50 ml/min of hydrogen gas at ambient pressure, the butene purifying tower was cooled to 50° C., and the reactor was cooled to 200° C.

Liquid trans-2-butene (purity 99%, Takachiho Chemical Industrial Co., Ltd.) distilled over γ-alumina (Sumitomo Chemical Co., Ltd., NKHD-32) before use was flowed into the butene purifying tower from the bottom at a rate of 0.10 g/min, using a plunger pump. The purified liquid trans-2-butene obtained from the top was combined with ethylene that had been pressurized to 3.5 MPa and was fed at a rate of 64.5 ml/min and hydrogen that had been pressurized to 3.5 MPa and was fed at a rate of 7.0 ml/min, and the mixture was fed, after passing through a preheating layer heated to 200° C., to the reactor from the top in the gas phase. The gas mixture obtained from the bottom of the reactor was brought to ambient pressure by passing through a back pressure valve and was analyzed on-line by gas chromatography. Based on the composition taken 10 hours after the reaction initiation, the butene conversion calculated by deducting the total amount of trans-2-butene, cis-2-butene and 1-butene in the gas at the outlet, from the amount of supplied trans-2-butene was 71%. The propylene selectivity at this time based on butene was 90%, and small amounts of pentene and hexene were generated in addition. Further, propane was generated together with propylene, and the ratio of propane/propylene was 0.01. The reaction was further carried out for another 12 hours, but no decrease in the conversion was observed.

Example 34

The reaction was carried out in the same manner as in Example 33, except that the temperature of the reactor was set at 175° C. The butene conversion obtained by analyzing the gas at the outlet taken 10 hours after the reaction initiation was 61%. The propylene selectivity was 92%, and small amounts of pentene and hexene were generated in addition. Further, propane was generated together with propylene, and the ratio of propane/propylene was 0.01. The reaction was further carried out for another 12 hours, but no decrease in the conversion was observed.

Example 35

The reaction was carried out in the same manner as in Example 33, except that the liquid trans-2-butene was combined with ethylene that had been pressurized to 1.0 MPa and hydrogen that had been pressurized to 1.0 MPa. The butene conversion obtained by analyzing the gas at the outlet taken 10 hours after the reaction initiation was 71%. The propylene selectivity was 91%, and small amounts of pentene and hexene were generated in addition. Further, propane was generated together with propylene, and the ratio of propane/propylene was 0.0026. The reaction was further carried out for another 12 hours, but no decrease in the conversion was observed.

Example 36

The reaction was carried out in the same manner as in Example 33, except that the liquid trans-2-butene was combined with ethylene that had been pressurized to 0.5 MPa and hydrogen that had been pressurized to 0.5 MPa. The butene conversion obtained by analyzing the gas at the outlet taken 10 hours after the reaction initiation was 72%. The propylene selectivity was 92%, and small amounts of pentene and hexene were generated in addition. Further, propane was generated together with propylene, and the ratio of propane/propylene was 0.0012. The reaction was further carried out for another 12 hours, but no decrease in the conversion was observed.

TABLE 9

Propylene synthesis reaction performed under pressure using WQ-10 and hydrotalcite

| Example | Reaction Temperature | Reaction Pressure (Gauge Pressure) | Butene Conversion | Propylene Selectivity | Propane/Propylene |
|---|---|---|---|---|---|
| 33 | 200° C. | 3.5 MPa | 71% | 90% | 0.010 |
| 34 | 175° C. | 3.5 MPa | 61% | 92% | 0.010 |
| 35 | 200° C. | 1.0 MPa | 71% | 91% | 0.0026 |
| 36 | 200° C. | 0.5 MPa | 72% | 92% | 0.0012 |

Example 37

15 g of γ-alumina (Sumitomo Chemical Co., Ltd., NKHD-32, surface area 250 m²/g) was suspended in a solution dissolving 0.08 g of sodium hydroxide (Wako Pure Chemical Industries, Ltd.) in 500 ml of distilled water at room temperature with stirring for 30 minutes, and water was evaporated off in an evaporator. The resulting white solid was calcined under an air atmosphere at 550° C. for 6 hours. The reaction was carried out in the same manner as in Example 33, except that 2.4 g of the obtained solid was used instead of hydrotalcite, and the reaction temperature was set at 175° C. The butene conversion obtained by analyzing the gas at the outlet taken 10 hours after the reaction initiation was 69%. The propylene selectivity was 94%, and small amounts of pentene and hexene were generated in addition. Further, propane was generated together with propylene, and the ratio of propane/propylene was 0.0066. The reaction was further carried out for another 12 hours, but no decrease in the conversion was observed.

TABLE 10

Propylene synthesis reaction performed under application of pressure using WQ-10 and alumina-supported $Na_2O$

| Example | Reaction Temperature | Reaction Pressure (Gauge Pressure) | Butene Conversion | Propylene Selectivity | Propane/ Propylene |
|---|---|---|---|---|---|
| 37 | 175° C. | 3.5 MPa | 69% | 94% | 0.0066 |

Example 38

0.1 g of WQ-10 and 0.5 g of hydrotalcite described in Example 1 were physically mixed and packed in the center of a reactor manufactured by SUS, having an external diameter of 10 mm and a length of 30 cm, with the top and bottom of the reactor packed with α-alumina balls. The resulting reactor was used as a reactor. On the other hand, 2 g of WQ-10 and 3.5 g of hydrotalcite (Kyowa Chemical Industry Co., Ltd., Kyowaad 500, 500 μm) were physically mixed and packed in a reactor manufactured by SUS, having an external diameter of 12 mm and a length of 40 cm, with the top and bottom of the reactor packed with α-alumina balls. The resulting reactor was used as a butene purifying tower. 50 ml/min of nitrogen gas at ambient pressure was flowed into the reactor from the top, and the gas exiting from the bottom of the reactor was flowed into the butene purifying tower from the bottom to the top. The temperatures of the reactor and the butene purifying tower were all elevated to 550° C. and maintained for 1 hour. Subsequently, a gas mixture obtained by adding 50 ml/min of hydrogen gas at ambient pressure to 50 ml/min of nitrogen gas at ambient pressure was flowed at the same temperature for 30 minutes. While flowing 50 ml/min of nitrogen gas at ambient pressure, the butene purifying tower was cooled to 50° C., and the reactor was cooled to 200° C.

1-Butene (purity 99%, containing 230 ppm of 1,3-butadiene, Takachiho Chemical Industrial Co., Ltd.) gas distilled over γ-alumina (Sumitomo Chemical Co., Ltd., NKHD-32) before use was flowed into the butene purifying tower from the bottom at ambient pressure at a rate of 8 ml/min. The concentration of 1,3-butadiene in the purified 1-butene obtained from the top was 0 ppm. This 1-butene containing no butadiene was combined with ethylene that was fed at ambient pressure at a rate of 12 ml/min and hydrogen that was fed at ambient pressure at a rate of 1 ml/min, and the mixture was fed to the reactor from the top in the gas phase. The gas mixture obtained from the bottom of the reactor was analyzed on-line by gas chromatography. Based on the composition taken 2 hours after the reaction initiation, the butene conversion calculated by deducting the total amount of trans-2-butene, cis-2-butene and 1-butene in the gas at the outlet, from the amount of supplied 1-butene was 17.5%. Further, propane was generated together with propylene, and the ratio of propane/propylene was 0.00022.

Example 39

The reaction was carried out in the same manner as in Example 38, except that the reaction temperature was set at 225° C. Based on the composition taken 3 hours after the reaction initiation, the butene conversion calculated by deducting the total amount of trans-2-butene, cis-2-butene and 1-butene in the gas at the outlet, from the amount of supplied 1-butene was 69%. The propylene selectivity was 94%, and small amounts of pentene and hexene were generated in addition. Further, propane was generated together with propylene, and the ratio of propane/propylene was 0.00047. The reaction was further carried out for another 12 hours, but no decrease in the conversion was observed.

Example 40

The reaction was carried out in the same manner as in Example 38, except that the reaction temperature was set at 250° C. Based on the composition taken 3 hours after the reaction initiation, the butene conversion calculated by deducting the total amount of trans-2-butene, cis-2-butene and 1-butene in the gas at the outlet, from the amount of supplied 1-butene was 69%. The propylene selectivity was 94%, and small amounts of pentene and hexene were generated in addition. Further, propane was generated together with propylene, and the ratio of propane/propylene was 0.00040. The reaction was further carried out for another 12 hours, but no decrease in the conversion was observed.

Example 41

The reaction was carried out in the same manner as in Example 38, except that the adsorbent in the butene purifying tower was changed to γ-alumina. The 1-butene fed to the reactor at this time contained 230 ppm of 1,3-butadiene. Based on the composition taken 3 hours after the reaction initiation, the butene conversion calculated by deducting the total amount of trans-2-butene, cis-2-butene and 1-butene in the gas at the outlet, from the amount of supplied 1-butene was 21%.

Example 42

The reaction was carried out in the same manner as in Example 41, except that the reaction temperature was set at 225° C. Based on the composition taken 3 hours after the reaction initiation, the butene conversion calculated by deducting the total amount of trans-2-butene, cis-2-butene and 1-butene in the gas at the outlet, from the amount of supplied 1-butene was 70%. The propylene selectivity was 94%, and small amounts of pentene and hexene were generated in addition. Further, propane was generated together with propylene, and the ratio of propane/propylene was 0.00036.

Example 43

The reaction was carried out in the same manner as in Example 41, except that the reaction temperature was set at 250° C. Based on the composition taken 3 hours after the reaction initiation, the butene conversion calculated by deducting the total amount of trans-2-butene, cis-2-butene and 1-butene in the gas at the outlet, from the amount of supplied 1-butene was 70%. The propylene selectivity was 94%, and small amounts of pentene and hexene were generated in addition.

TABLE 11

Propylene synthesis reaction performed using a raw material containing 230 ppm of butadiene and using WQ-10 and hydrotalcite

| Example | Reaction Temperature | Butadiene concentration in 1-butene fed to the reactor | Butene Conversion |
|---------|----------------------|---------------------------------------------------------|-------------------|
| 38 | 200° C. | 0 | 17% |
| 39 | 225° C. | 0 | 69% |
| 40 | 250° C. | 0 | 69% |
| 41 | 200° C. | 230 ppm | 21% |
| 42 | 225° C. | 230 ppm | 70% |
| 43 | 250° C. | 230 ppm | 70% |

Example 44

The reaction was carried out at 200° C. in the same manner as in Example 38, except that the catalyst packed in the reactor was changed to 0.1 g of WQ-10 and 0.5 g of γ-alumina-supported $Na_2O$ produced in Example 18. Based on the composition taken 3 hours after the reaction initiation, the butene conversion calculated by deducting the total amount of trans-2-butene, cis-2-butene and 1-butene in the gas at the outlet, from the amount of supplied 1-butene was 69%. The propylene selectivity was 93%, and small amounts of pentene and hexene were generated in addition. Further, propane was generated together with propylene, and the ratio of propane/propylene was 0.00021.

Example 45

The reaction was carried out in the same manner as in Example 44, except that the adsorbent in the butene purifying tower was changed to γ-alumina. The 1-butene fed to the reactor at this time contained 230 ppm of 1,3-butadiene. Based on the composition taken 3 hours after the reaction initiation, the butene conversion calculated by deducting the total amount of trans-2-butene, cis-2-butene and 1-butene in the gas at the outlet, from the amount of supplied 1-butene was 69%. The propylene selectivity was 93%, and small amounts of pentene and hexene were generated in addition. Further, propane was generated together with propylene, and the ratio of propane/propylene was 0.00019.

TABLE 12

Propylene synthesis reaction using a raw material containing 230 ppm of butadiene and using WQ-10 and γ-alumina-supported $Na_2O$

| Example | Reaction Temperature | Butadiene concentration in 1-butene fed to the reactor | Butene Conversion |
|---------|----------------------|---------------------------------------------------------|-------------------|
| 44 | 200° C. | 0 | 69% |
| 45 | 200° C. | 230 ppm | 69% |

Example 46

The reaction was carried out in the same manner as in Example 41, except that the reaction was carried out at 250° C. using a raw material comprising 1,3-butadiene mixed in at a ratio of 2 g with respect to 200 g of 1-butene. The 1-butene fed to the reactor at this time contained 1.04% of 1,3-butadiene. Based on the composition taken 10 hours after the reaction initiation, the butene conversion calculated by deducting the total amount of trans-2-butene, cis-2-butene and 1-butene in the gas at the outlet, from the amount of supplied 1-butene was 67%.

Example 47

The reaction was carried out in the same manner as in Example 46, except that the reaction was carried out at 275° C. Based on the composition taken 5 hours after the reaction initiation, the butene conversion rate calculated by deducting the total amount of trans-2-butene, cis-2-butene and 1-butene in the gas at the outlet, from the amount of supplied 1-butene was 68%.

Example 48

The reaction was carried out in the same manner as in Example 46, except that the reaction was carried out at 300° C. Based on the composition taken 3 hours after the reaction initiation, the butene conversion calculated by deducting the total amount of trans-2-butene, cis-2-butene and 1-butene in the gas at the outlet, from the amount of supplied 1-butene was 68%.

Example 49

The reaction was carried out in the same manner as in Example 44, except that the reaction was carried out at 250° C. using a raw material comprising 1,3-butadiene mixed in at a ratio of 2 g with respect to 200 g of 1-butene. The 1-butene fed to the reactor at this time contained 1.04% of 1,3-butadiene. Based on the composition taken 20 hours after the reaction initiation, at which time the maximum activity was achieved, the butene conversion calculated by deducting the total amount of trans-2-butene, cis-2-butene and 1-butene in the gas at the outlet, from the amount of supplied 1-butene was 58%. No propane generation was confirmed at this time.

Example 50

The reaction was carried out in the same manner as in Example 49, except that the reaction was carried out at 275° C. Based on the composition taken 15 hours after the reaction initiation, at which time the maximum activity was achieved, the butene conversion calculated by deducting the total amount of trans-2-butene, cis-2-butene and 1-butene in the gas at the outlet, from the amount of supplied 1-butene was 68%. No propane generation was confirmed at this time.

Example 51

The reaction was carried out in the same manner as in Example 49, except that the reaction was carried out at 300° C. Based on the composition taken 2 hours after the reaction initiation, at which time the maximum activity was achieved, the butene conversion calculated by deducting the total amount of trans-2-butene, cis-2-butene and 1-butene in the gas at the outlet, from the amount of supplied 1-butene was 69%. No propane generation was confirmed at this time.

TABLE 13

Propylene synthesis reaction performed using butene containing 1.04% of 1,3-butadiene

| Example | Catalyst | Reaction Temperature | Butene Conversion |
|---|---|---|---|
| 46 | WQ-10 + hydrotalcite | 250° C. | 67% |
| 47 | | 275° C. | 68% |
| 48 | | 300° C. | 68% |
| 49 | WQ-10 + γ-alumina- | 250° C. | 58% |
| 50 | supported Na$_2$O | 275° C. | 68% |
| 51 | | 300° C. | 69% |

Example 52

A butene purifying tower was produced in the same manner as in Example 1, except that 2 g of WQ-10 and then 3.5 g of hydrotalcite (Kyowa Chemical Industry Co., Ltd., Kyowaad 500, 500 μm) were successively packed from the bottom of the butene purifying tower. Subsequently, a reactor was produced in the same manner, except that the catalyst packed in the reactor was changed from the mixture of WQ-10 and hydrotalcite to a mixture of WQ-10 and Na$_2$O/magnesia which was obtained by suspending 15 g of magnesium oxide and 80 mg of sodium hydroxide in 200 ml of an aqueous solution, drying by evaporation, and calcining (550° C.×8 hours), which was packed in the reactor. Subsequently, 50 ml/min of nitrogen gas at ambient pressure was flowed into the reactor from the top, and the gas exiting from the bottom was flowed into the butene purifying tower from the bottom to the top. The temperatures of the reactor and the butene purifying tower were all elevated to 550° C. and maintained for 1 hour. Next, a gas mixture formed by adding 50 ml/min of hydrogen gas at ambient pressure to 50 ml/min of nitrogen gas at ambient pressure was flowed at the same temperature for 30 minutes. While flowing again 50 ml/min of nitrogen gas at ambient pressure, the butene purifying tower was cooled to 150° C., and the reactor was cooled to 175° C.

1-Butene (purity 99%, Takachiho Chemical Industrial Co., Ltd.) gas distilled over γ-alumina (Sumitomo Chemical Co., Ltd., NKHD-32) before use was flowed into the butene purifying tower from the bottom at ambient pressure at a rate of 12 ml/min. The purified 1-butene obtained from the top was combined with ethylene that was fed at ambient pressure at a rate of 18 ml/min and hydrogen that was fed at ambient pressure at a rate of 1.5 ml/min, and the mixture was fed to the reactor from the top in the gas phase. The gas mixture obtained from the bottom of the reactor was analyzed on-line by gas chromatography. Based on the composition taken 3 hours after the reaction initiation, the butene conversion calculated by deducting the total amount of trans-2-butene, cis-2-butene and 1-butene in the gas at the outlet, from the amount of supplied 1-butene was 40%.

Example 53

The reaction was carried out in the same manner as in Example 52, except that the catalyst packed in the reactor was changed from the mixture of WQ-10 and hydrotalcite to a mixture of WQ-10 and Na$_2$O/hydrotalcite which was obtained by suspending 15 g of hydrotalcite (Kyowa Chemical Industry, Ltd., Kyowaad 500) and 80 mg of sodium hydroxide in 200 ml of an aqueous solution, drying to solid by evaporation, and calcining (550° C.×8 hours). The gas mixture obtained from the bottom of the reactor was analyzed on-line by gas chromatography. Based on the composition taken 3 hours after the reaction initiation, the butene conversion calculated by deducting the total amount of trans-2-butene, cis-2-butene and 1-butene in the gas at the outlet, from the amount of supplied 1-butene was 52%.

Example 54

The reaction was carried out in the same manner as in Example 52, except that the catalyst packed in the reactor was changed from the mixture of WQ-10 and hydrotalcite to a mixture of WQ-10 and Na$_2$O/alumina.magnesia which was obtained by suspending 15 g of an alumina.magnesia solid solution (Kyowa Chemical Industry, Ltd., Kyowaad 2000) and 40 mg of sodium hydroxide in 200 ml of an aqueous solution, drying to solid by evaporation, and calcining (550° C.×8 hours). The gas mixture obtained from the bottom of the reactor was analyzed on-line by gas chromatography. Based on the composition taken 3 hours after the reaction initiation, the butene conversion calculated by deducting the total amount of trans-2-butene, cis-2-butene and 1-butene in the gas at the outlet, from the amount of supplied 1-butene was 58%.

Example 55

The reaction was carried out in the same manner as in Example 52, except that the catalyst packed in the reactor was changed from the mixture of WQ-10 and hydrotalcite to a mixture of WQ-10 and K$_2$O/alumina.magnesia which was obtained by suspending 15 g of an alumina.magnesia solid solution (Kyowa Chemical Industry, Ltd., Kyowaad 2000) and 40 mg of potassium nitrate in 200 ml of an aqueous solution, drying to solid by evaporation, and calcining (550° C.×8 hours). The gas mixture obtained from the bottom of the reactor was analyzed on-line by gas chromatography. Based on the composition taken 3 hours after the reaction initiation, the butene conversion calculated by deducting the total amount of trans-2-butene, cis-2-butene and 1-butene in the gas at the outlet, from the amount of supplied 1-butene was 62%.

TABLE 14

Propylene synthesis reaction performed at 175° C. using WQ-10 and various co-catalysts

| Example | Kind of co-catalyst support | Kind of metal supported on co-catalyst (Amount determined from the introduced weight) | Butene Conversion |
|---|---|---|---|
| 52 | Magnesium oxide (Kyowamag 150) | Sodium oxide (0.5%) | 40% |

TABLE 14-continued

Propylene synthesis reaction performed at 175° C. using WQ-10 and various co-catalysts

| Example | Kind of co-catalyst support | Kind of metal supported on co-catalyst (Amount determined from the introduced weight) | Butene Conversion |
|---|---|---|---|
| 53 | Hydrotalcite (Kyowaad 500) | Sodium oxide (0.5%) | 52% |
| 54 | Magnesium oxide•aluminum oxide solid solution (Kyowaad 2000) | Sodium oxide (0.25%) | 58% |
| 55 | Magnesium oxide•aluminum oxide solid solution (Kyowaad 2000) | Potassium oxide (0.125%) | 62% |

Comparative Example 1

The pretreatment, reduction treatment and nitrogen purge were carried out with the same reactor and butene purifying tower as those used in Example 1, and then without flowing hydrogen through the reactor, ethylene and trans-2-butene were fed to the reactor at the same rates as those used in Example 1. The butene conversion obtained by analyzing the gas at the outlet taken 3 hours after the reaction initiation was 49%. The propylene selectivity based on butene at this time was 91%, and a small amount of pentene was generated in addition.

Comparative Example 2

The pretreatment, reduction treatment and nitrogen purge were carried out with the same reactor and butene purifying tower as those used in Example 4, and then without flowing hydrogen through the reactor, ethylene and trans-2-butene were fed to the reactor at the same rates as those used in Example 1. The butene conversion obtained by analyzing the gas at the outlet taken 3 hours after the reaction initiation was 1%. The propylene selectivity based on butene at this time was 89%, and a small amount of pentene was generated in addition.

Comparative Example 3

The pretreatment, reduction treatment and nitrogen purge were carried out with the same reactor and butene purifying tower as those used in Comparative Example 2, and then without flowing hydrogen through the reactor, ethylene and trans-2-butene were fed to the reactor at the same rates as those used in Example 1, and the operation was carried out in the same manner, except that the reaction temperature was set at 300° C. The butene conversion obtained by analyzing the gas at the outlet taken 3 hours after the reaction initiation was 74%. The propylene selectivity based on butene at this time was 95%, and a small amount of pentene was generated in addition.

Comparative Example 4

The pretreatment, reduction treatment and nitrogen purge were carried out with the same reactor and butene purifying tower as those used in Example 31, and then without flowing hydrogen through the reactor, ethylene and trans-2-butene were fed to the reactor at the same rates as those used in Example 1. The butene conversion obtained by analyzing the gas at the outlet taken 1 hour after the reaction initiation was 8%.

Comparative Example 5

The pretreatment, reduction treatment and nitrogen purge were carried out with the same reactor and butene purifying tower as those used in Example 32, and then without flowing hydrogen through the reactor, ethylene and trans-2-butene were fed to the reactor at the same rates as those used in Example 1. The butene conversion obtained by analyzing the gas at the outlet taken 1 hour after the reaction initiation was 22%.

Comparative Example 6

The pretreatment, reduction treatment and nitrogen purge were carried out with the same reactor and butene purifying tower as those used in Example 33, and then with a nitrogen flow rate of 100 ml/min, the butene purifying tower was cooled to 50° C., and the reactor was cooled to 200° C. Without flowing hydrogen through the reactor, ethylene and trans-2-butene were fed to the reactor at the same rates as those used in Example 34. The butene conversion obtained by analyzing the gas at the outlet taken 10 hours after the reaction initiation was 7.8%.

Comparative Example 7

The pretreatment and reduction treatment were carried out with the same reactor and butene purifying tower as those used in Example 33, and then with a nitrogen flow rate of 100 ml/min, the butene purifying tower was cooled to 50° C., and the reactor was cooled to 250° C. Without flowing hydrogen through the reactor, ethylene and trans-2-butene were fed to the reactor at the same rates as those used in Example 34. The butene conversion obtained by analyzing the gas at the outlet taken 1 hour after the reaction initiation was 71%.

TABLE 15

Propylene synthesis reaction performed without allowing hydrogen gas to co-exist with the raw material

| Comp. Ex. | Name of Catalyst | Kind of Co-catalyst | Reaction Temperature | Pressure | Butene Conversion |
|---|---|---|---|---|---|
| 1 | WQ-10 | Hydrotalcite | 250° C. | Ambient pressure | 49% |
| 2 | Same as above | Same as above | 200° C. | Same as above | 1% |
| 3 | Same as above | Same as above | 300° C. | Same as above | 74% |
| 4 | MoQ-15 | Same as above | 300° C. | Same as above | 8% |
| 5 | Same as above | Same as above | 350° C. | Same as above | 22% |

TABLE 15-continued

Propylene synthesis reaction performed without allowing hydrogen gas to co-exist with the raw material

| Comp. Ex. | Name of Catalyst | Kind of Co-catalyst | Reaction Temperature | Pressure | Butene Conversion |
|---|---|---|---|---|---|
| 6 | WQ-10 | Same as above | 200° C. | 3.5 MPa | 7.8% |
| 7 | Same as above | Same as above | 250° C. | Same as above | 71% |

Comparative Example 8

The pretreatment and reduction treatment were carried out with the same reactor and butene purifying tower as those used in Example 38, and then with a nitrogen flow rate of 100 ml/min, the butene purifying tower was cooled to 50° C., and the reactor was cooled to 275° C. Without flowing hydrogen through the reactor, ethylene and 1-butene were fed to the reactor at the same rates as those used in Example 38. The butene conversion obtained by analyzing the gas at the outlet taken 1 hour after the reaction initiation was 44%.

Comparative Example 9

The reaction was carried out in the same manner as in Comparative Example 8, without allowing hydrogen to co-exist in the reactor, except that the adsorbent in the butene purifying tower was changed to γ-alumina. The 1-butene fed to the reactor at this time contained 230 ppm of butadiene. The butene conversion obtained by analyzing the gas at the outlet taken 1 hour after the reaction initiation was 38%. After 5 hours of the reaction initiation, significant catalyst deterioration was observed.

Comparative Example 10

The reaction was carried out in the same manner as in Comparative Example 8, without allowing hydrogen to co-exist in the reactor, except that the reaction temperature was set at 300° C. The butene conversion obtained by analyzing the gas at the outlet taken 1 hour after the reaction initiation was 61%.

Comparative Example 11

The reaction was carried out in the same manner as in Comparative Example 9, without allowing hydrogen to co-exist in the reactor, except that the reaction temperature was set at 300° C. The butene conversion obtained by analyzing the gas at the outlet taken 1 hour after the reaction initiation was 47%. After 5 hours of the reaction initiation, significant catalyst deterioration was observed.

Comparative Example 12

The reaction was carried out in the same manner as in Example 46, using butene containing 1.04% of butadiene as the raw material, except that the reaction temperature was set at 300° C., and no hydrogen gas was fed to the reactor. The butene conversion obtained by analyzing the gas at the outlet taken 1 hour after the reaction initiation was 17%.

Comparative Example 13

The reaction was carried out in the same manner as in Comparative Example 12, without supplying hydrogen to the reactor, except that the reaction temperature was set at 350° C. The butene conversion obtained by analyzing the gas at the outlet taken 1 hour after the reaction initiation was 68%. That is, when a raw material containing 1.04% of butadiene was used, it is difficult to obtain a conversion exceeding 60% if the reaction temperature is not elevated to 350° C., as shown by the present Comparative Example, while a raw material containing no butadiene achieves a conversion of 61% at 300° C. as shown by Comparative Example 10.

TABLE 16

Propylene synthesis reaction performed using a raw material containing butadiene and using WQ-10 and hydrotalcite

| Comp. Ex. | Reaction Temperature | Butadiene concentration in 1-butene fed to the reactor | Butene Conversion |
|---|---|---|---|
| 8 | 275° C. | 0 | 44% |
| 9 | 275° C. | 230 ppm | 38% |
| 10 | 300° C. | 0 | 61% |
| 11 | 300° C. | 230 ppm | 47% |
| 12 | 300° C. | 1.04% | 17% |
| 13 | 350° C. | 1.04% | 68% |

Reference Example 1

The pretreatment and reduction treatment were carried out with the same reactor and butene purifying tower as those used in Example 1, and when nitrogen purge was carried out, a gas mixture of nitrogen/hydrogen=1/1 instead of nitrogen gas was used to cool the reactor and the butene purifying tower to a predetermined temperature, and without flowing hydrogen through the reactor, ethylene and trans-2-butene were fed to the reactor at the same rates as those used in Example 1. The butene conversion obtained by analyzing the gas at the outlet taken 1 hour after the reaction initiation was 75%. The butene conversion obtained by analyzing the gas at the outlet taken 5 hours after the reaction initiation was 48%. Furthermore, the reaction was further continued for another 12 hours, but no change in the conversion was observed.

As such, the metathesis reaction can be carried out at lower temperatures compared with conventionally known reactions, by allowing hydrogen gas to co-exist in the reaction raw materials. Furthermore, sufficient reaction rates can be achieved even at low pressures, without particularly requiring high pressure as conventional reactions do. In addition, even when butene containing butadiene is used as a raw material, the invention is characterized in that the deterioration of the catalyst is less compared with the case of conventional metathesis catalysts. As another feature, there is responsiveness to the improvement in the reaction activity through hydrogen supply. That is, when the hydrogen supply is temporarily suspended and resumed later, the effect of improving the activity through hydrogen addition is restored. Such behavior can significantly contribute to the operation stability in industrial production. Furthermore, when olefins and hydrogen gas are usually allowed to co-exist, there would be fear for side production of paraffins; however, in contrast to the prediction, side production of paraffins is less, and particularly when a co-catalyst of alumina-supported sodium oxide is used, the side production paraffins can be reduced to a large extent.

The invention claimed is:

1. A process of producing olefins through a metathesis reaction of reacting homologous or heterologous olefins to produce olefins having different structures, wherein the reaction is carried out in the co-existence of hydrogen gas and in the presence of a catalyst containing at least one metal element selected from tungsten and molybdenum having a structure of being supported only on silica and a compound containing at least one metal element selected from the metals of Group Ia (alkali metals), Group IIa (alkaline earth metals), Group IIb or Group IIIa as a co-catalyst in addition to the catalyst.

2. The process of producing olefins according to claim 1, wherein the co-catalyst has a structure of being supported on a support.

3. The process of producing olefins according to claim 2, wherein the support supporting the co-catalyst is alumina or zirconia.

4. The process of producing olefins according to claim 1, wherein at least one of the metal elements contained in the co-catalyst is lithium, sodium, potassium, magnesium, calcium, yttrium or zinc.

5. The process of producing olefins according to claim 4, wherein at least one of the metal elements contained in the co-catalyst is lithium, sodium or potassium.

6. The process of producing olefins according to claim 1, wherein propylene is obtained by reacting ethylene with n-butene.

7. The process of producing olefins according to claim 1, wherein the amount of hydrogen gas to co-exist with the raw materials fed to the reactor is, when the amount of the raw materials is in terms of gas, 0.1 to 80% by volume based on the total amount of gas.

8. The process of producing olefins according to claim 1, wherein the co-catalyst is a compound selected from the group consisting of magnesium oxide, calcium oxide, yttrium oxide, zinc oxide, hydrotalcite and a solid solution of aluminum oxide and magnesium oxide.

9. The process of producing olefins according claim 1, wherein the amount of the co-catalyst with respect to the catalyst is between 0.1 and 20.

* * * * *